United States Patent [19]

Bitensky et al.

[11] Patent Number: 5,624,794
[45] Date of Patent: Apr. 29, 1997

[54] METHOD FOR EXTENDING THE USEFUL SHELF-LIFE OF REFRIGERATED RED BLOOD CELLS BY FLUSHING WITH INERT GAS

[75] Inventors: Mark W. Bitensky; Tatsuro Yoshida, both of Los Alamos, N.M.

[73] Assignee: The Regents of the University of California, Los Alamos, N.M.

[21] Appl. No.: 473,675

[22] Filed: Jun. 5, 1995

[51] Int. Cl.$^6$ .............................. A01N 1/02; A61M 37/00
[52] U.S. Cl. .................................................. 435/2; 604/4
[58] Field of Search ................................. 435/2; 604/4

[56] References Cited

U.S. PATENT DOCUMENTS

| | | | |
|---|---|---|---|
| 4,902,701 | 2/1990 | Batchelor et al. | 514/381 |
| 5,476,764 | 12/1995 | Bitensky | 435/2 |

OTHER PUBLICATIONS

Högman CF et al, Biomed. Biochim. Acta 42:S327–331 (1983).
Högman CF et al., Biomed. Biochim Acta 46:S290–294 (1987).
T.J. Greenwalt et al., "Studies In Red Blood Cell Preservation-7. In Vivo and in Vitro Studies With A Modified Phosphate–Ammonium Additive Solution," Vox Sang 65, 87–94 (1993).
E. Beutler et al., "Storage Of Red Cell Concentrates In CPD–A2 For 42 and 49 Days," J. Lab. Clin. Med. 102, pp. 53–62 (1983).
Högman et al., "Effects Of Oxygen On Red Cells During Liquid Storage at +4°C," Vox Sang, 51, 27–34 (1986).

*Primary Examiner*—John W. Rollins
*Assistant Examiner*—S. Saucier
*Attorney, Agent, or Firm*—Samuel M. Freund

[57] ABSTRACT

Method using oxygen removal for extending the useful shelf-life of refrigerated red blood cells. A cost-effective, 4° C. storage procedure that preserves red cell quality and prolongs post-transfusion in vivo survival is described. Preservation of adenosine triphosphate levels and reduction in hemolysis and in membrane vesicle production of red blood cells stored at 4° C. for prolonged periods of time is achieved by removing oxygen therefrom at the time of storage; in particular, by flushing with an inert gas. Adenosine triphosphate levels of the stored red blood cells are boosted in some samples by addition of ammonium phosphate.

13 Claims, 4 Drawing Sheets

METHOD FOR EXTENDING THE USEFUL SHELF-LIFE OF REFRIGERATED RED BLOOD CELLS BY FLUSHING WITH INERT GAS

FIELD OF THE INVENTION

The present invention relates generally to the liquid preservation of blood and, more particularly, to the refrigerated storage of blood in the absence of oxygen. The invention was made with government support under Contract No. W-7405-ENG-36 awarded by the U.S. Department of Energy to the Regents of The University of California. The government has certain rights in the invention.

BACKGROUND OF THE INVENTION

The current blood supply is considerably smaller than the need therefor. Stored blood is considered unusable after about 5–6 weeks of steady deterioration in storage as determined by the inability of such cells to survive in the circulation after transfusion, which in part is caused by hemoglobin oxidation and degradation and adenosine triphosphate (ATP) depletion. Moreover, the risks involved in receiving blood from nonautologous donors remains significant. In order to address current needs, blood storage techniques must be simple, inexpensive and long-term.

Red blood cells (RBCs) survive for about 4 months under conditions of turbulent flow in the body without protein synthesis. Oxygen ($O_2$) is essential for the conversion of hemoglobin (Hb) to met-Hb, the breakdown of which produces toxic products such as hemichrome, heroin and free $Fe^{3+}$. Together with $O_2$, these products catalyze the formation of hydroxyl radicals (OH•), and both OH• and the met-Hb breakdown products damage the red cell lipid membrane, the membrane skeleton, and the cell contents. As will be discussed hereinbelow, current approaches to red cell preservation do not address the hemoglobin breakdown damage pathway.

Refrigeration reversibly disables the enzymes essential for met-Hb reduction in vivo, increases the solubility of damaging $O_2$ (almost by a factor of 2) in the environment of the red blood cells, and permits the level of ATP to decrease by diminishing the glycolytic rate (at 4° C. the rate is about 1% of that found at 37° C.). Reduction of red cell ATP concentration results in echinocyte (an unstable form of red blood cells) formation, increased rates of membrane vesiculation, loss of red cell surface area, and accelerated sequestration by splenic macrophages. Vesiculation continues throughout the cold storage period, is exacerbated by echinocyte formation, and decreases red blood cell survival by decreasing red blood cell membrane area.

The effects of elevation and preservation of ATP levels in blood storage situations has been studied. For example, in "Studies In Red Blood Cell Preservation-7. In Vivo and in Vitro Studies With A Modified Phosphate-Ammonium Additive Solution," by Greenwalt et al., Vox Sang 65, 87–94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5–6 weeks to an improved standard of 8–9 weeks. Packed RBCs are suitable for transfusion following the removal of the supernatant with a single washing step. Greenwalt et al. also conclude that factors other than ATP concentration appear to play an increasingly important role in determining RBC viability after 50 days of storage. They cite the results of L. Wood and E. Beutler in "The Viability Of Human Blood Stored In Phosphate Adenine Media," Transfusion 7, 401–408 (1967), find in their own experiments that the relationship between ATP concentration and 24-hour RBC survival measurements appears to become less clear after about 8 weeks of storage. E. Beutler and C. West restate that the relationship between red cell ATP concentration and viability is a weak one after prolonged periods of storage in "Storage Of Red Cell Concentrates In CPD-A2 For 42 and 49 Days," J. Lab. Clin. Med. 102, 53–62 (1983).

In "Effects Of Oxygen On Red Cells During Liquid Storage at +4° C.," by Högman et al., Vox Sang 51, 27–34 (1986), the authors discuss that red cell content of ATP is slightly better maintained at anaerobic than at aerobic storage after 2–3 weeks. Venous blood was refrigerated and deprived of additional oxygen during storage, by placing the oxygen-permeable storage bags in a nitrogen environment and thereby gradually reducing the level of oxygen saturation. The reduction in oxygen concentration occurs slowly during storage at 4° C., and is far from complete, starting at ~60% and reaching ~30% hemoglobin saturation at 5 weeks. No conclusion could be drawn concerning the effects of this procedure on the overall quality of stored cells. These authors did not address or significantly reduce the oxygen-dependent damage to hemoglobin and the oxygen-mediated damage caused by hemoglobin breakdown products.

Accordingly, it is an object of the present invention to provide a procedure for blood storage which addresses the problems of hemoglobin degradation, red blood cell lysis (hemolysis) and ATP depletion in a manner consistent with the practice of autologous transfusion and enhanced heterologous transfusion logistics, and which achieves significant prolongation of the time during which refrigerated storage of red blood cells is not detrimental to their subsequent use.

Another object of the present invention is to provide a procedure for prolonged blood storage while minimizing the complexity of the procedures required for preparing transfusible samples.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for storing red blood cells hereof includes the steps of: mixing a sample of whole blood containing the red blood cells to be stored with an anticoagulant solution, forming thereby a first suspension of red blood cells, concentrating the red blood cells from the liquid portion (plasma) of the first suspension, forming thereby a mass of packed red blood cells, mixing the packed red blood cells so produced with an additive solution which includes glucose, adenine, and salts, forming thereby a second suspension of red blood cells, removing the oxygen from the second suspension of red blood cells, and cooling the second suspension of red blood cells to 4° C.

Preferably, no further exposure of the cooled red blood cells to oxygen is permitted.

In another aspect of the present invention, and in accordance with its objects and purposes, the method for storing red blood cells hereof includes the steps of: forming a mass of packed red blood cells, mixing the packed red blood cells with an additive solution which includes glucose, adenine, and salts, forming thereby a suspension of red blood cells removing the oxygen from the suspension of red blood cells, and cooling the suspension of red blood cells to 4° C.

Preferably, no further exposure of the cooled red blood cells to oxygen is permitted.

Benefits and advantages of the present invention include the preservation of ATP levels and the reduction of hemolysis and accumulation of membrane vesicles in the refrigerated RBCs, as a consequence of creating an environment ($O_2$ removal) that prevents hemoglobin degradation, with the result that useful refrigerated storage periods may be prolonged.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Briefly, the present invention includes improvement of the in vivo survival characteristics of transfused red blood cells that have been stored at 4° C. for prolonged periods of time by removing oxygen therefrom at the time of storage, and preventing any further exposure of the stored RBCs to oxygen. The in vitro diagnostics of hemolysis, vesicle production and ATP levels, when taken together, provide a useful indication of in vivo survival. Moreover, adenosine triphosphate levels within the stored red blood cells have been boosted in some samples by addition of ammonium phosphate.

Oxygen removal, and the effects of various additive solutions were investigated with red blood cells stored in standard polyvinyl chloride (PVC) blood bags with di-(2-ethylhexyl) phthalate (DEHP) plasticizer containing citrate, phosphate, sodium chloride, adenine, and dextrose (anticoagulant/buffer solution, AS3) after centrifugation. Oxygen was removed from the warm RBCs by flushing the blood bags with argon 7-10 times, which reduced the oxygen level of the RBCs to between 8% and 5%, respectively, of their saturation levels. Each unit of blood was sub-divided (about 120 mL aliquots) into pediatric DEHP plasticized PVC transfer bags with 150 mL capacity. Blood was stored at 4° C. in a light-shielded blood bank refrigerator and samples were withdrawn via a sterile septum sampling port. Rapid cooling after rapid purging is essential to prevent lactic acid buildup in the RBCs. Moreover, it should be mentioned that the oxygen can also be removed after the RBCs are cooled. However, since the RBCs are unprotected from the effects of oxidation once cooled, and since oxygen removal is more rapid at 37° C. or 21° C. when compared with 4° C., the preferred procedure is to cool them after oxygen removal. As reported by H Ögman et al., supra, conventional PVC blood storage bags are permeable to $O_2$. It takes about 4 weeks of conventional storage for a unit of packed red blood cells to become fully oxygenated. In order to evaluate the long-term effects of replacing the storage gas, transfer bags were stored in an anaerobic chamber filled with an inert gas such as argon. Blood bag gas exchange was further enhanced by 2–3 cycles of exposing the anaerobic chamber to partial vacuum followed by filling with the appropriate gas. In addition, a hydrogen generating system with a palladium catalyst was placed in the anaerobic chamber that houses the stored blood to continuously remove emerging traces of $O_2$.

The effect of ammonium phosphate additive solution for boosting ATP called EAS2 and described by Greenwalt et al., supra, was further investigated by the present inventors. As stated above, this additive produces a gradual elevation of ATP which is sustained by the red blood cells during extended periods of storage at 4° C.

Figure 1:
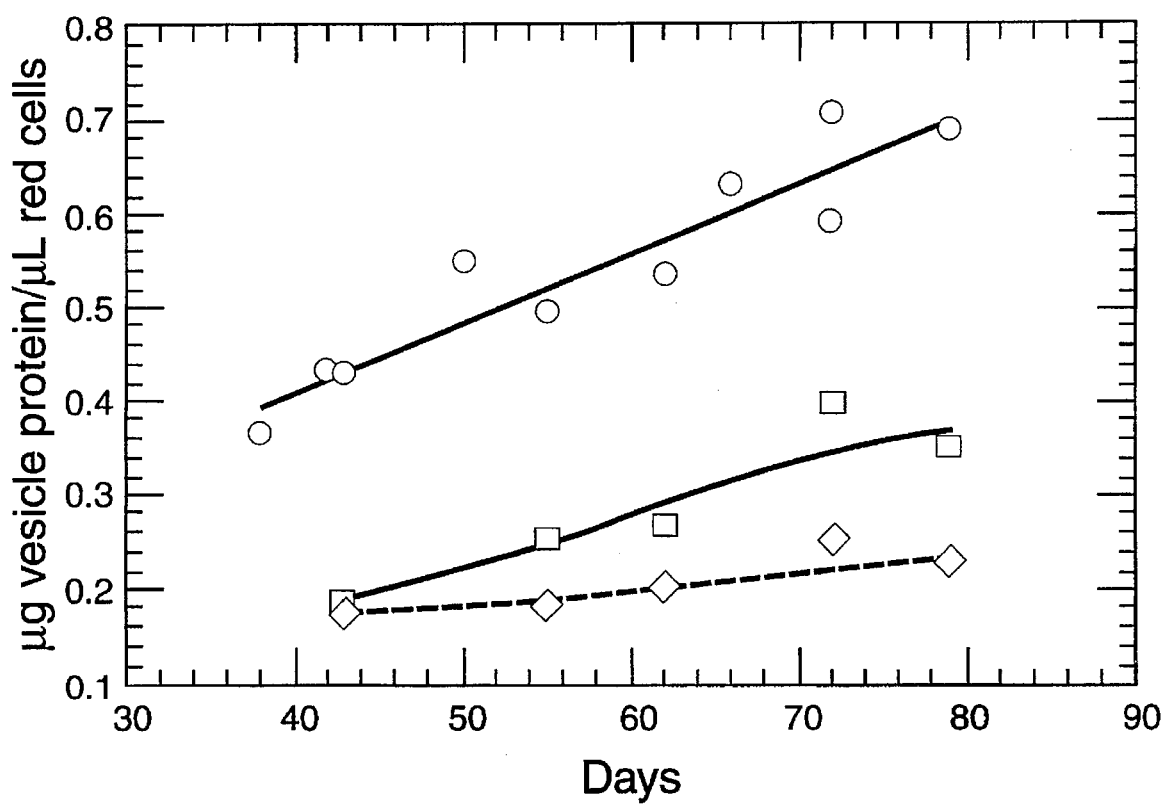
FIG. 1 shows the effect of different storage gases as a function of time on the quantity of membrane vesicles accumulated during storage of red blood cells treated with ammonium phosphate at 4° C.

Reference will now be made in detail to the present preferred embodiments of the present invention, examples of which are illustrated in the accompanying drawings. Turning now to FIG. 1, the effect of different storage gases as a function of time on the accumulation of membrane vesicles during storage of red blood cells treated with ammonium phosphate at 4° C. is shown. The amounts of protein obtained in the form of membrane vesicles that are released by red blood cells during storage with AS3 (open circles), EAS2 (Xs), and EAS2 plus argon (+s) are presented. Data points represent the average of 5 individuals. The addition of 10 mM $NH_4^+$ as $NH_4Cl$ and 20 mM $PO_4^{-3}$ as $Na_2HPO_4$ (EAS2), appreciably elevated ATP levels and decreased vesicle production throughout the storage period. It is seen that removal of $O_2$ with argon and an $O_2$ scavenger ($H_2$/Pd) further decreases the vesicle production. Oxygen removal with argon in the presence of $(NH_4)_3PO_4$ also reduced rates of hemolysis and further boosted ATP levels above the levels achieved with the addition of $(NH_4)_3PO_4$ in the absence of $O_2$ removal.

Figure 2:
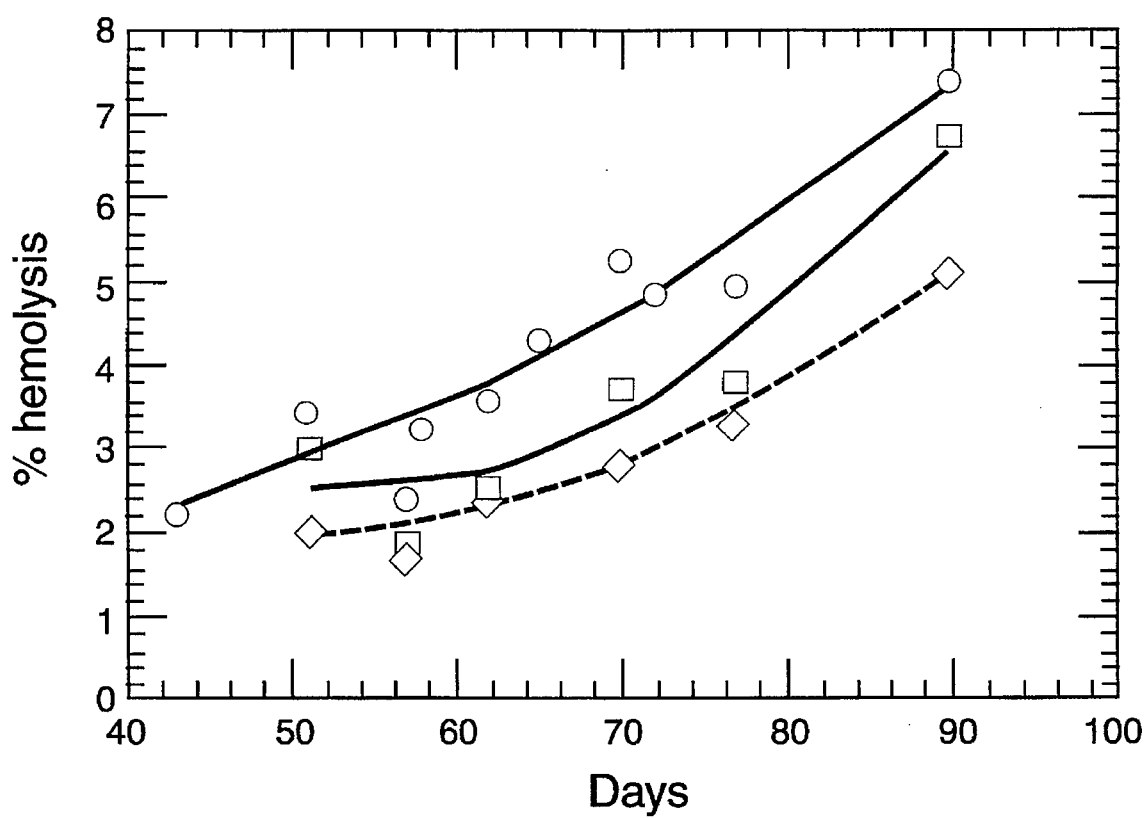
FIG. 2 shows the effect of different storage gases as a function of time on the rates of hemolysis during storage of red blood cells treated with ammonium phosphate at 4° C.

FIG. 2 shows the effect of different storage gases as a function of time on the rate of hemolysis during storage of red blood cells treated with ammonium phosphate at 4° C. Percent hemolysis with AS3 (open circles), EAS2 (Xs), and EAS2 plus Ar (+s) are presented. Data points represent the average value of 10 (AS3) or 5 (others) individuals. The extent of hemolysis in all samples was somewhat higher than expected for banked blood as a consequence of the inversion and mixing that is required prior to repeated sampling of refrigerated RBCs for the in vitro diagnostics. It is again clearly seen that the percent hemolysis improves when the RBC suspension is deprived of oxygen.

Figure 3:
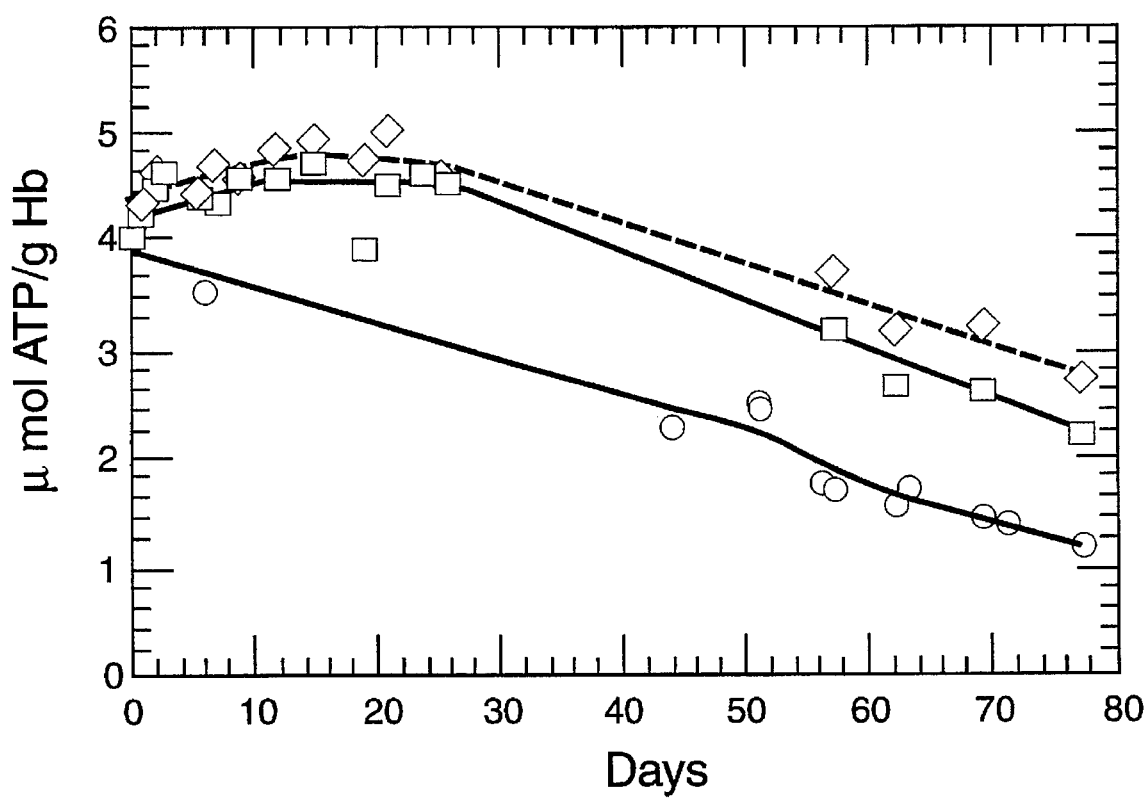
FIG. 3 shows the effect of different storage gases as a function of time on the cellular ATP levels during storage of red blood cells at 4° C. in the presence and absence of ammonium phosphate.

FIG. 3 shows the effect of different storage gases as a function of time on the ATP concentration during storage of red blood cells at 4° C. in the presence and absence of ammonium phosphate. Total cellular ATP is given as µmol ATP/g Hb. Symbols are: AS3 control (open circles), EAS2 (Xs), and EAS2 plus argon (+s). Data points represent average values for 5–10 individuals. Oxygen-depleted samples sustained even higher levels of ATP than those with the $(NH_4)_3PO_4$ additive, over the 11 weeks investigated.

Having generally described the invention, the following example sets forth the details of the method hereof.

EXAMPLE

Figure 4:
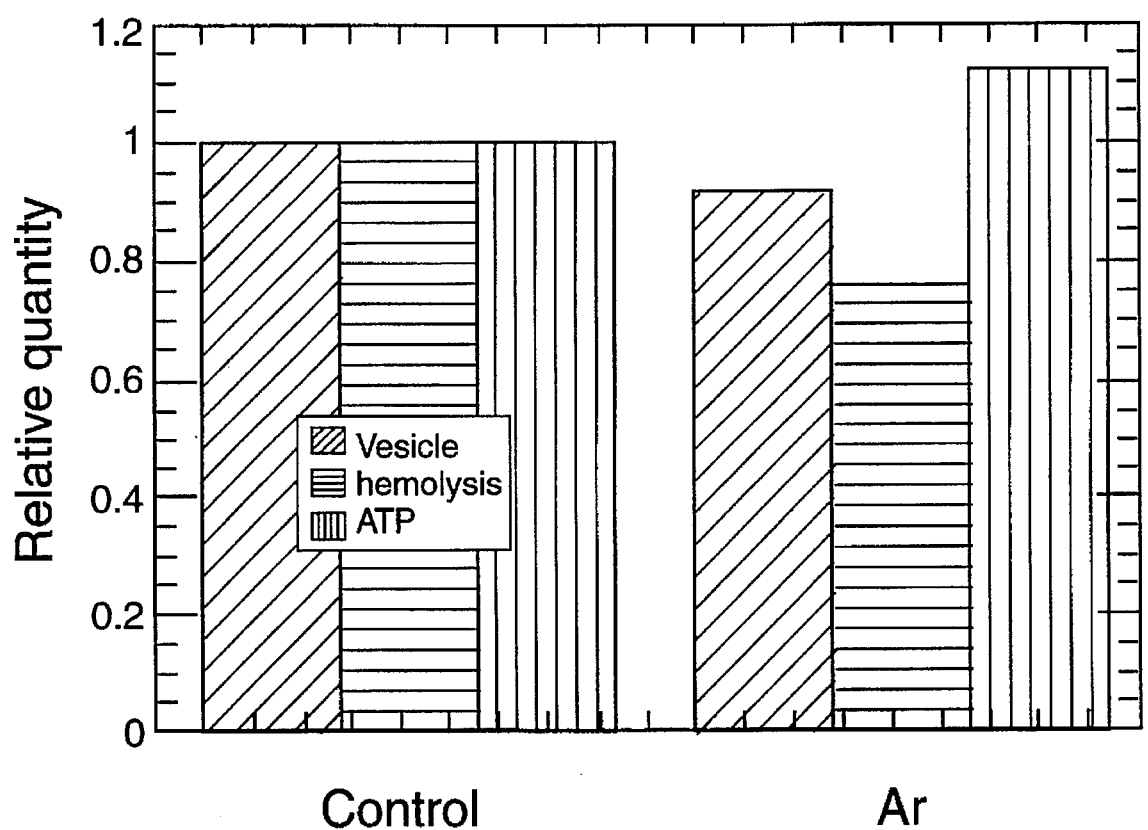
FIG. 4 shows the effect of oxygen removal on total red blood cell ATP, extent of hemolysis, and quantity of shed vesicles for red blood cells stored for 3.5 weeks at 4° C., relative to an untreated control sample.

FIG. 4 shows the effect of oxygen removal on total red blood cell ATP, extent of hemolysis, and quantity of shed vesicles for red blood cells stored for 3.5 weeks at 4° C., relative to an untreated control sample. Six units of packed red blood cells were stored in Adsol or AS3 preserving solutions for 3–4 days at a commercial blood bank. Approximately equal volumes of ultra-pure Ar were introduced into the blood bag containing ~300 mL of cells at 22° C. and horizontally and gently agitated (40 rpm). The gas was exchanged 7 times over a 4 hour period, at which point the oxygen saturation of hemoglobin was measured to be ~5%. The cells were then placed in 150 mL transfer bags housed in gas-tight canisters containing 90% Ar, 10% $H_2$, and a palladium catalyst. The blood was maintained at 4° C. It is readily observed that all of the indicia of in vivo survival are improved by the removal of oxygen only. The results are understated, since the blood samples employed had already been chilled in the presence of oxygen for 2–4 days.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for storing red blood cells which comprises the steps of:
   a. mixing a sample of whole blood containing the red blood cells to be stored with an anticoagulant solution, forming thereby a first suspension of red blood cells;
   b. concentrating the red blood cells from the liquid portion of the first suspension, forming thereby a mass of packed red blood cells;
   c. mixing the packed red blood cells so produced with an additive solution which comprises glucose, adenine, and salts, forming thereby a second suspension of red blood cells;
   d. reducing the oxygen level of the red blood cells in the second suspension of red blood cells to approximately 8% or less of their saturation level by flushing the red blood cells with an inert gas; and
   e. storing the red blood cells in the second suspension of red blood cells at 4° C.

2. The method for storing red blood cells as described in claim 1, further comprising the step of storing the second suspension of red blood cells in an oxygen-permeable container which is located in an oxygen-free environment.

3. The method for storing red blood cells as described in claim 1, further comprising the step of storing the second suspension of red blood cells in an oxygen-permeable container which is located in an oxygen-free environment containing oxygen scavenging materials.

4. The method for storing red blood cells as described in claim 1, further comprising the step of adding ammonium phosphate to the second suspension to boost adenosine triphosphate levels in the red blood cells.

5. The method for storing red blood cells as described in claim 1, wherein said step of reducing the level of oxygen in the red blood cells of the second suspension takes place before said step of storing the red blood cells in the second suspension at 4° C.

6. The method for storing red blood cells as described in claim 4, further comprising the step of washing the red blood cells with a saline solution containing glucose before their use in order to lower the concentration of ammonium phosphate therein.

7. A method for storing red blood cells which comprises the steps of:
   a. forming a mass of packed red blood cells;
   b. mixing the packed red blood cells with an additive solution which comprises glucose, adenine, and salts, forming thereby a suspension of red blood cells;
   c. reducing the oxygen level of the red blood cells in the suspension of red blood cells to approximately 8% or less of their saturation level by flushing the red blood cells with an inert gas; and
   d. storing the red blood cells in the suspension of red blood cells at 4° C.

8. The method for storing red blood cells as described in claim 7, further comprising the step of storing the suspension of red blood cells in an oxygen-permeable container which is located in an oxygen-free environment.

9. The method for storing red blood cells as described in claim 7, further comprising the step of storing the suspension of red blood cells in an oxygen-permeable container which is located in an oxygen-free environment containing oxygen scavenging materials.

10. The method for storing red blood cells as described in claim 7, further comprising the step of adding ammonium phosphate to the suspension to boost adenosine triphosphate levels in the red blood cells.

11. The method for storing red blood cells as described in claim 7, wherein said step of reducing the level of oxygen in the red blood cells in the suspension takes place before said step of storing the red blood cells in the suspension at 4° C.

12. The method for storing red blood cells as described in claim 10, further comprising the step of washing the red blood cells with a saline solution containing glucose before their use in order to lower the concentration of ammonium phosphate therein.

13. A method for storing red blood cells which comprises the steps of:
   a. mixing a sample of whole blood containing the red blood cells to be stored with an anticoagulant solution, forming thereby a first suspension of red blood cells;
   b. concentrating the red blood cells from the liquid portion of the first suspension, forming thereby a mass of packed red blood cells;
   c. mixing the packed red blood cells so produced with an additive solution which comprises glucose, adenine, and salts, forming thereby a second suspension of red blood cells;
   d. reducing the oxygen level of the red blood cells in the second suspension of red blood cells to approximately 8% or less of their saturation level by flushing the red blood cells with an inert gas; and
   e. storing the red blood cells in the second suspension of red blood cells at 4° C. in a gas permeable container which is located in an oxygen-free environment.

* * * * *